US012624013B2

(12) United States Patent
Beheshti Tabar et al.

(10) Patent No.: US 12,624,013 B2
(45) Date of Patent: May 12, 2026

(54) PURIFICATION OF 2,5-FURANDICARBOXYLIC ACID, DIMETHYL ESTER AND OTHER ESTERIFIED PRODUCTS

(71) Applicant: Archer Daniels Midland Company, Decatur, IL (US)

(72) Inventors: Iman Beheshti Tabar, Decatur, IL (US); Kenneth F. Stensrud, Decatur, IL (US); William Christopher Hoffman, Decatur, IL (US)

(73) Assignee: ARCHER-DANIELS-MIDLAND COMPANY, Decatur, IL (US)

( * ) Notice: Subject to any disclaimer, the term of this patent is extended or adjusted under 35 U.S.C. 154(b) by 461 days.

(21) Appl. No.: 18/041,394

(22) PCT Filed: Jul. 29, 2021

(86) PCT No.: PCT/US2021/043728
§ 371 (c)(1),
(2) Date: Feb. 10, 2023

(87) PCT Pub. No.: WO2022/035610
PCT Pub. Date: Feb. 17, 2022

(65) Prior Publication Data
US 2023/0348410 A1 Nov. 2, 2023

Related U.S. Application Data

(60) Provisional application No. 63/064,872, filed on Aug. 12, 2020.

(51) Int. Cl.
*C07D 307/68* (2006.01)
*C07B 63/00* (2006.01)

(52) U.S. Cl.
CPC ............ *C07D 307/68* (2013.01); *C07B 63/00* (2013.01)

(58) Field of Classification Search
CPC .............................. C07D 307/68; C07B 63/00
USPC ......................................................... 549/485
See application file for complete search history.

(56) References Cited

U.S. PATENT DOCUMENTS 9,169,229 B2 10/2015 Parker et al.
2008/0182944 A1 7/2008 Benecke et al.
2013/0345448 A1 12/2013 Shaikh et al.
2015/0119588 A1 4/2015 van Haveren et al.
2016/0075672 A1 3/2016 van Haveren et al.
2017/0320845 A1 11/2017 De Sousa Dias et al.
2018/0155307 A1 6/2018 Metkar et al.
2018/0179173 A1* 6/2018 Cipot-Wechsler ... C07D 307/68
2019/0031634 A1 1/2019 Metkar et al.

FOREIGN PATENT DOCUMENTS

| | | |
|---|---|---|
| CN | 105246958 A | 1/2016 |
| CN | 108299352 A | 7/2018 |
| CN | 110799504 A | 2/2020 |
| EP | 3647310 A1 | 5/2020 |
| JP | 2008088134 A | 4/2008 |
| KZ | 33364 B | 11/2018 |
| RU | 2699640 C2 | 9/2019 |
| WO | WO 2013-191942 | 12/2013 |
| WO | 2015155784 A1 | 10/2015 |
| WO | WO 2016-076712 | 5/2016 |
| WO | 2017019431 A1 | 2/2017 |
| WO | WO 2017-019441 | 2/2017 |
| WO | 2019072920 A1 | 4/2019 |
| WO | 2022035610 A1 | 2/2022 |

OTHER PUBLICATIONS

Xiong, R. et al., "Evaluation of COSMO-SAC method for the prediction of the alcohol-water partition coefficients of the compounds encountered in aqueous phase fructose dehydration", Chemical Engineering Science, 2015, vol. 126, pp. 169-176; the whole document.
Thiyagarajan, S., et al., "Concurrent formation of furan-2,5- and furan-2,4-dicarboxylic acid: unexpected aspects of the Henkel reaction", RSC Advances, The Royal Society of Chemistry, vol. 3, Issue. 36, pp. 15678-15686 (2013).

* cited by examiner

*Primary Examiner* — Taylor V Oh
(74) *Attorney, Agent, or Firm* — Jesse S. Harper

(57) ABSTRACT

Methods are disclosed for the purification of crude compositions comprising 2,5-furandicarboxylic acid, dimethyl ester (FDME) or other diester derivatives (e.g., dialkyl ester derivatives) of 2,5-furandicarboxylic acid (FDCA), by crystallization. In this regard, certain solvents, and classes of solvents, have been discovered to promote the selective crystallization of FDME over impurities often generated in its production by FDCA esterification and other upstream processing steps. Importantly, certain impurities that are selectively removed include those that would otherwise be detrimental to the color and/or color stability of the purified composition. Other improvements in crystallization reside in the use of techniques such as liquid-liquid extraction and pre-treatment of the crystallization solution by contact with a solid medium.

15 Claims, No Drawings

PURIFICATION OF 2,5-FURANDICARBOXYLIC ACID, DIMETHYL ESTER AND OTHER ESTERIFIED PRODUCTS

CROSS-REFERENCE TO RELATED APPLICATIONS

This application is a national stage entry of International Application No. PCT/US21/043728, filed Jul. 29, 2021, which itself claims priority to U.S. Provisional Patent Application No. 63/064,872, filed Aug. 12, 2020, the contents of each are incorporated herein by reference.

FIELD OF THE INVENTION

The present invention relates to methods for the purification of biobased monomers, and particularly esterified monomers such as 2,5-furandicarboxylic acid, dimethyl ester (FDME), which are useful in producing biobased polymers such as poly(alkylene terephthalate) polymers.

BACKGROUND OF THE INVENTION

The depletion of fossil fuels has created major incentives for seeking alternative sources to petroleum-based carbon for the synthesis of so-called "platform" molecules that can serve as the building blocks for commercially significant products. Biomass is currently viewed as a potential replacement from which many such high value chemicals can be derived, but the development of sustainable technologies for the production of such chemicals from renewable resources remains a significant challenge.

The biobased monomers, 2,5-furandicarboxylic acid (FDCA) and its methyl ester derivative, 2,5-furandicarboxylic acid, dimethyl ester (FDME) are recognized as important starting materials in the production of poly(alkylene furandicarboxylate) polymers that can substitute for their known, mass-produced petroleum derived analogs, namely poly(alkylene terephthalate) polymers, such as polyethylene terephthalate (PET). A prominent example of a biobased poly(alkylene furandicarboxylate) polymer is poly(ethylene furandicarboxylate), or PEF, obtained by reaction of FDCA or FDME with ethylene glycol. This biobased plastic exhibits superior properties in a number of respects, relative to its petroleum-derived analog, PET, particularly in the area of packaging. For example, blends of PEF and PET can provide improved barrier properties with respect to $CO_2$ and $O_2$, prolonging shelf life over pure PET and providing an acceptable container for products such as beer that are susceptible to oxidative degradation. Other packaging applications of PEF include films used to manufacture pouches, wrappers, and heat shrink materials having high mechanical strength and recyclability.

In general, both FDCA and FDME are useful platform molecules in the production of polyamides, polyurethanes, and polyesters having diverse applications as plastics, fibers, coatings, adhesives, personal care products, and lubricants. A significant consideration with respect to polymers that are made from these monomers is their color and color stability, i.e., resistance to color degradation over time, particularly resulting from exposure to a combination of heat and oxygen (e.g., air). Color, or more appropriately the absence of color, is important for applications such food packaging and particularly beverage bottle manufacturing, in which a lack of transparency or possibly yellowness in the plastic are readily perceived and often equated to an inferior product. To this end, it has been recognized that the use of the esterified monomer, FDME, affords advantages over FDCA in terms of resulting in better color of the final poly(alkylene furan dicarboxylate) polymer, as well as a greater ease in handling and processing. Color improvement through esterification may at least partly result from improved stability of esterified product, in terms of preventing aldol condensation reactions that might otherwise occur.

Known processes for converting FDCA to its dialkyl ester derivative (e.g., its dimethyl ester derivative, FDME) by reaction with an appropriate alcohol (e.g., methanol) are disclosed, for example in WO 2017/019431, and such methods include post-reaction crystallization steps to increase FDME purity. A reactive distillation process for the esterification of FDCA is disclosed in US 2019/0031634, whereby distillation is combined with the esterification reaction in an effort to provide an FDME product with increased purity. On the other hand, U.S. Pat. No. 9,169,229 describes a series of steps to obtain a purified FDME (termed "DMFD") and other esterified derivatives, and such steps include physical separation (e.g., distillation to drive off excess alcohol) and solid-liquid separation, with optional drying or crystallization. Disclosed compositions are purported to have improved color and a reduced concentration of impurities, including not more than 0.8 wt-% of 5-formyl-2-furancarboxylic acid methyl ester (termed "methyl 5-formylfuran-2-carboxylate").

Improvements in the quality of FDME and other diester derivatives of FDCA are key to the overall effort in establishing poly(alkylene furandicarboxylate) polymers as commercially viable alternatives to their petroleum-based counterparts. Despite the efforts to date, however, obtaining such diester derivatives with sufficient purity remains a considerable challenge, especially in terms of the manufacture of biobased plastic end products having color characteristics that would be accepted in the marketplace.

SUMMARY

More specifically, the present invention has been developed in consideration of a number of practical difficulties encountered in the purification of FDME and other diester derivatives of FDCA by distillation as suggested in the cited art. Such difficulties can include equipment fouling; development of color in, and agglomeration of, the purified composition; low yields; loss of valuable unconverted and partially converted compounds; and the need for pre- and post-treatment processing steps, among others.

By means of the present invention, alternative methods are thus provided (to distillation) for the purification of crude compositions comprising 2,5-furandicarboxylic acid, dimethyl ester (FDME) or one or more other diester derivatives (e.g., dialkyl ester derivatives) of 2,5-furandicarboxylic acid (FDCA), involving crystallization from a solvent.

Advantageously, certain solvents, and classes of solvents, have been discovered to promote the selective crystallization of FDME over impurities that would otherwise be detrimental to the color and/or color stability of the purified composition.

This discovery further permits the use of purification methods, described in detail hereafter, that do not subject the crude compositions or solutions formed from these crude compositions, to the temperatures normally required for the distillation of FDME, even under vacuum conditions. Such temperatures can independently result in thermal degradation and the formation of impurities that directly contribute to color or contribute to reduced color stability of the desired FDME over time.

According to particular, non-limiting embodiments making use of this discovery, crystallization may be combined with aqueous-organic (liquid-liquid) extraction performed on a solution of the crude composition (e.g., in the case of extractive crystallization), and/or may be combined with passing the solution through, or otherwise contacting it with, a solid treatment medium, such as to remove solids and/or improve color.

Processes are therefore described herein for purifying a crude composition comprising predominantly FDME or one or more diester derivatives of FDCA more generally (e.g., the diethyl ester derivative of FDCA or the diphenyl ester derivative of FDCA), according to which certain solvents are employed and/or one or both of a biphasic solution and a solid treatment medium are utilized. These processes can advantageously provide a purified composition, or optionally a second-stage purified composition, third-stage purified composition, or higher-stage purified composition (e.g., following multiple stages of crystallization, optionally in combination with extraction, and/or treatment), which is exceptional in terms of its purity, color characteristics (e.g., colorless appearance), rheological properties (e.g., freely flowing crystals), and color stability.

"Purity" in this context may be defined in terms of the presence (e.g., a high weight percentage) of a compound of interest (FDME or other diester derivative of FDCA). Alternatively, "purity" may be meaningfully defined in terms of the absence (e.g., a low weight percentage) of impurities that result from methods used to produce FDME or other diester derivatives of FDCA, and particularly those impurities that undesirably lead to color formation initially and/or over time.

Color stability may be exhibited, for example, by the maintenance of a colorless appearance even after storage under ambient conditions (e.g., in air at approximately room temperature) for an extended period, which may be up to several years. Further advantages of processes described herein reside in high yield or recovery of the compound of interest, as well as overall simplicity, particularly in comparison to techniques involving distillation or other approaches requiring elevated temperatures, such as greater than 100° C.

DETAILED DESCRIPTION OF EMBODIMENTS

The terms "wt-%" and "wt-ppm," as used herein, are used to designate percentage by weight and parts per million by weight, respectively.

Throughout this disclosure, processes are described in terms of their use for purifying 2,5-furandicarboxylic acid, dimethyl ester (FDME), for example being present in a crude solid composition obtained from an esterification reaction of 2,5-furan dicarboxylic acid (FDCA) with methanol. It can be appreciated that such processes can be readily extended to other diester derivatives (e.g., dialkyl ester derivatives) obtained from the esterification of FDCA with other alcohols such as ethanol, propanol, or phenol, whether such diester derivatives are explicitly mentioned or not alongside the 2,5-furandicarboxylic acid, dimethyl ester (FDME) that is of principal (but not sole) interest.

Regardless of the particular esterification, however, there will be some degree of inefficiency observed in the esterification reaction, as manifest by incomplete conversion and/or byproduct formation. Reaction inefficiencies are likewise inevitable in those other processing steps that have been contemplated in the art as occurring upstream of esterification, including for example and in particular, in the dehydrating of carbohydrates (e.g., hexose sugars) to generate FDCA-forming furanics, such as 5-hydroxymethylfurfural (HMF), and in the oxidizing of these FDCA-forming furanics to generate a crude composition including FDCA.

As a result, crude compositions comprising, as a compound of interest, FDME or another diester derivative of FDCA, inevitably and unavoidably further comprise impurities, such as (i) aldehyde derivatives and (ii) aldehyde-ester (e.g., aldehyde-alkyl ester) derivatives of FDCA, at least some of which can lead to color formation initially and/or over time.

In the case of (i), one of the carboxylic acid groups of FDCA is replaced with an aldehyde group, and, in the case of (ii), one of the carboxylic acid groups of FDCA is replaced with an aldehyde group and the other of the carboxylic acid groups is an ester derivative of carboxylic acid, with this ester derivative being the same type of ester derivative (e.g., methyl ester derivative) as that of the compound of interest (FDME or other diester derivative of FDCA). Other impurities may include (iii) partially-esterified, or partially converted, compounds such as monoester derivatives of FDCA, in which one of the carboxylic acid groups is an ester derivative of carboxylic acid, with this ester derivative being the same type of ester derivative (e.g., methyl ester derivative) as that of the compound of interest, as well as (iv) unconverted FDCA. Further impurities may include metals and their metallic salts, such as salts of metallic cations of Co, Ca, Mn, Sn, Na and/or salts of anions of Br, P, fumarate, which may originate from a homogeneous or heterogeneous catalyst used to carry out the esterification reaction.

The impurities described above, in crude compositions, result from methods that are used to produce FDME or other diester derivatives of FDCA. Often, the crude composition exhibits poor color characteristics, meaning that it may differ significantly from being white or colorless in appearance, such as in the case of being yellow, brown, or even black in color, though the crude composition having poor color characteristics may in fact contain only very small quantities of a given impurity and even very small quantities of all impurities taken together.

Representative crude compositions comprising FDME or other diester derivative of FDCA may thus comprise this compound of interest (i.e., provide a compound to be further purified pursuant to the present invention) in an amount of at least 70 wt-% (e.g., from 70 wt-% to 98 wt-%), such as at least 75 wt-% (e.g., from 75 wt-% to 95 wt-%) or at least 80 wt-% (e.g., from 80 wt-% to 90 wt-%). Such compositions may comprise an impurity according to (i) above (e.g., 5-formyl-2-furandicarboxylic acid (FFCA)) in an amount from 1 wt-% down to as little as 0.01 wt-%, such from 0.5 wt-% down to 0.03 wt-% or from 0.2 wt-% down to 0.05 wt-%. Such compositions may independently comprise, or further comprise, an impurity according to (ii) above (e.g., 5-formyl-2-furandicarboxylic acid methyl ester (FFME)) in an amount from 2 wt-% down to 0.1 wt-%, such from 1 wt-% down to 0.2 wt-% or from 0.8 wt-% down to 0.3 wt-%. Such compositions may independently comprise, or further comprise, an impurity according to (iii) above (e.g., 2,5-furandicarboxylic acid, monomethyl ester (FDMME)) in an amount from 20 wt-% down to 3 wt-%, such from 15 wt-% down to 5 wt-% or from 12 wt-% down to 8 wt-%. Such compositions may independently comprise, or further comprise, an impurity according to (iv) above, namely FDCA, in an amount from 2 wt-% down to 0.05 wt-%, such from 1 wt-% down to 0.1 wt-%, or from 0.8 wt-% down to 0.2 wt-%. Such compositions may independently comprise, or further comprise, other impurities such as metals and/or their metallic salts as described above, in an amount from 12 wt-% down to 0.5 wt-%, such from 10 wt-% down to 1 wt-%, or from 8 wt-% down to 3 wt-%.

Advantageously, processes as described herein may include utilizing or recycling of at least a portion of the partially converted and unconverted compounds (or impurities according to (iii) and/or (iv) above) back to an esterification reactor, to improve overall esterification performance. For example, recycling can improve the overall conversion of FDCA and the overall yield of FDME or other diester derivative of FDCA, relative to the respective per-pass conversion and per-pass yield obtained in the esterification reactor (i.e., in a single pass of the reactants through this reactor). As esterification performance approaches the ideal case of recycling partially converted and unconverted compounds to extinction, overall conversion in the esterification reactor approaches 100% and the overall yield approaches the reaction selectivity.

In view of the above description, it can be appreciated that, according to particular embodiments in which the dialkyl ester derivative FDME is of interest for recovery in the purified composition, particular color-forming impurities to be removed in the purified composition (or to be reduced in concentration relative to their concentration in the crude composition) are (i) 5-formyl-2-furandicarboxylic acid (FFCA) and (ii) 5-formyl-2-furandicarboxylic acid methyl ester (FFME). Other impurities are (iii) partially-esterified, or partially converted, 2,5-furandicarboxylic acid, monomethyl ester (FDMME) and (iv) unconverted FDCA, which are valuable intermediates and unconverted feed components, respectively, therefore having the potential to improve overall esterification performance, as described above.

As previously mentioned, the alternative (to distillation) purification methods with which the present application is concerned proceed from the discovery of certain solvents in which the compound of interest (FDME or other diester derivative of FDCA) is particularly soluble and which promote the selective crystallization of this compound upon cooling. That is, a purified solid composition may be recovered from crystallization, having an increased content or percentage by weight of the compound of interest, relative to the crude composition.

A representative process making use of this discovery comprises dissolving a crude FDCA ester composition in a solvent to form a solution of the crude composition, and crystallizing (or selectively crystallizing), from the solution of the crude composition, a purified composition having an increased content of FDME, or of the other diester derivative of FDCA, relative to the crude composition. According to such embodiments, the solvent differs from conventional solvents in that it is not the particular alcohol used to esterify FDCA, in obtaining the compound of interest, or at least does not contain this alcohol in any significant amount (e.g., this alcohol is present in the solvent in an amount of less than 10 wt-%, less than 5 wt-%, or less than 1 wt-%).

For example, in the case of FDME being the compound of interest, this is obtained from the esterification of FDCA with methanol, and the solvent may therefore be termed a "non-methanol" solvent, which contains no methanol, or at least does not contain methanol in any significant amount as described above. Representative non-methanol solvents are organic solvents, such as those that will form two distinct phases when combined with an equal volume of water.

Solvents of this type may be, more specifically, non-alcohol solvents, which contain no compounds having hydroxy (—OH) functional groups, such as alcohols, diols, polyols, and glycols, or at least do not contain such compounds in any significant amount as described above. Alternatively, or in combination, in preferred solvents the compound of interest (FDME or other diester derivative of FDCA) has a solubility at 35° C. of at least 10 wt-% (e.g., from 10 wt-% to 45 wt-%), at least 12 wt-% (e.g., from 12 wt-% to 40 wt-%), or at least 15 wt-% (e.g., from 15 wt-% to 30 wt-%). According to some embodiments, the solvent may comprise a halogenated hydrocarbon, a nitrile, an amide, a heterocyclic ring-containing compound, an acetate, a ketone, or a sulfoxide. The solvent may, for example comprise a particular compound within one of these classes in a predominant amount (e.g., in an amount of at least 50 wt-%, at least 75 wt-%, at least 90 wt-%, at least 95 wt-%, or at least 99 wt-%). The solvent may comprise a mixture of compounds within these classes (so that "solvent" will be clearly understood as encompassing a plurality of chemically distinct solvent species in combination, if the wording admits of both the possibility of a single solvent species or a plurality of solvent species) and/or among these different classes, with such mixture being present in the solvent in such predominant amount. Exemplary solvents may comprise one or more of methylene chloride; acetonitrile; N,N'-dimethylformamide; 1,4-dioxane; 1,1,2,2-tetrachloroethane; ethyl acetate; tetrahydrofuran; pyridine; acetone; and dimethyl sulfoxide, which may be present in the solvent, alone or in combination, in such predominant amount. A particularly preferred solvent is methylene chloride due to a favorable combination of properties, in terms of the solubility of the compound of interest (e.g., FDME) and its selective crystallization from impurities as described herein.

The solution of the crude composition, which is formed by dissolving the crude composition in the solvent (e.g., for FDME, a non-methanol solvent as described above), may be more specifically formed by dissolving the crude composition in the solvent at an elevated temperature, such as a temperature from 25° C. to the normal boiling point of the solvent, or, in the case of the solvent being a mixture, to the normal boiling point of the compound in such mixture having the lowest boiling point. For example, this elevated temperature may be from 25° C. to 100° C., such as from 25° C. to 80° C. or from 30° C. to 50° C.

As described above, purifying crude compositions according to the distillation-alternative processes described herein advantageously avoids the elevated temperatures to which the crude composition or solution of this composition would otherwise be subjected (in the use of distillation as the prior art has proposed) for purifying these compositions. For example, the steps of dissolving and crystallizing may be carried out at a temperature of less than 130° C., less than 100° C., less than 80° C., less than 60° C., or even less than 40° C. Preferably, all steps of dissolving and crystallizing, in the case of particular processes utilizing two or more stages of crystallization, are carried out at such temperatures. In more specific embodiments, in any of the processes for purifying a crude composition as described herein, the entire process is carried out at such temperatures, i.e., at no point in the process such temperature exceeded. By limiting the maximum temperature, a formation of color and/or a reduction in color stability in the purified composition, which might otherwise result at higher temperatures, may be diminished or avoided altogether.

Following the formation of the solution, such as by dissolving the crude composition in a solvent as described above, the step of crystallizing may be carried out by cooling this solution, optionally in combination with evaporating the solvent, for example under vacuum pressure. The cooling temperate profile may be selected to balance objectives of processing efficiency and obtaining crystals of a desired size and/or size distribution. The solution may be cooled, for example, to a minimum temperature of less than 20° C., less than 15° C., less than 10° C., or less than 5° C., with this minimum temperature, in any of these cases, being attained after a time of at least 1 hour, at least 2 hours, at least 3 hours, at least 4 hours, at least 6 hours, at least 8 hours, at least 10 hours, at least 20 hours, or at least 24 hours, after cooling is initiated. The cooling results in the crystallization of the purified composition, in solid form, having an increased content or percentage by weight of the compound of interest (FDME or other diester derivative of FDCA) and a decreased content or percentage by weight of one or more impurities, such as the impurities (i), (ii), (iii), and (iv) as described above, and/or a decreased content or percentage by weight of metals and/or their metallic salts as described above.

Following any step of crystallizing, as described herein, whether this involves crystallizing the purified composition in a first stage of crystallization, crystallizing a second-stage purified composition having an increased content or percentage by weight of the compound of interest (e.g., FDME or other diester derivative of FDCA) relative to both the purified composition and crude composition, or crystallizing a higher-stage purified composition, such step(s) of crystallization are typically, and preferably, followed by recovering such purified composition(s). This involves separating such purified composition(s) as a solid, for example as in the case of recovering such purified composition(s) as a solid residue in a filtration step, from their respective mother liquor(s). Recovering of such purified composition(s) may involve additional steps of rinsing (e.g., with additional wash portions of solvent) and/or drying. Processes having two or more stages of crystallization may therefore include steps of crystallizing purified compositions at each stage, with successive crystallizing steps yielding compositions having a successively increasing purity, or percentage by weight, of the compound of interest. The recovering of such purified compositions at all stages except the last stage is followed by re-dissolving such purified compositions in respective, additional quantities of solvent, which may be referred to as a second-stage solvent, a third stage solvent, etc. These additional quantities generally have the same composition as the solvent used in the first stage to dissolve the crude composition. However, the use of solvents having different components, or differing amounts of the same components, is also contemplated.

In other embodiments, processes for purifying a crude composition comprising a compound of interest (FDME or other diester derivative of FDCA) combine crystallization with the use of liquid-liquid extraction of a solution of the crude composition. Representative processes comprise forming a biphasic solution of the crude composition in a solvent comprising an organic phase and a separate aqueous phase. Such processes further comprise separating the organic phase from the aqueous phase and crystallizing, from the organic phase, a purified composition having characteristics as described herein (e.g., an increased content or percentage by weight of FDME or other diester of FDCA). The organic phase, as part of the biphasic solution, may comprise, or may have the composition of, any organic solvent as described above. The organic phase is not limited by excluding alcohols and may therefore comprise (e.g., in a predominant amount as described above), one or more compounds having at least one hydroxy (—OH) functional group, such as an alcohol (e.g., methanol), a diol, a polyol, and/or a glycol. The biphasic solution may be formed, for example, by dissolving the crude composition in the organic phase to form a solution of the crude composition, followed by adding the aqueous phase to this solution. Alternatively, the components for forming the biphasic solution may be added in other orders, such as combining the aqueous phase with the crude composition prior to dissolving the crude composition in the organic phase, or combining the organic and aqueous phases, prior to adding the crude composition. In the case of forming a biphasic solution, the organic phase may be easily separated from the aqueous phase, such as by removing the more dense phase (e.g., the organic phase) through the bottom of a separatory device, prior to crystallizing, from the organic phase, the purified composition. The step of crystallizing may be carried out as described above, for example according to a cooling temperature profile having a minimum temperature that is achieved over a time period, within the parameters given above.

In such an extraction, or extractive crystallization process, one or more impurities in the crude composition (e.g., one or more of impurities (i), (ii), (iii), and (iv) as described above) are selectively solubilized in the aqueous phase, relative to the compound of interest (FDME or other diester of FDCA) in the crude composition. The compound of interest is selectively solubilized in the organic phase, relative to the one or more impurities in the crude composition. For a given compound to be selectively solubilized in a given phase, a greater proportion of that compound, originally present in the crude composition, is solubilized in that given phase, compared to the other phase. The aqueous phase may be water or, in preferred embodiments, an aqueous salt solution that aids in the selective solubilization of the one or more impurities (e.g., FDMME and/or FDCA) into this phase, for example by ionizing carboxylic acid groups of these impurities. A preferred salt solution is a sodium bicarbonate solution, although solutions of other salts, such as salts of alkali and alkaline earth metals (e.g., Na, K, Mg, Ca, Sr, Ba) as well as salts of other metals, including their carbonate, bicarbonate, nitrate, sulfate, halide (e.g., chloride), phosphate, or other salts, may also be used as the aqueous phase, with such salts being present alone or in combination in the salt solution/aqueous phase.

Particularly in the case of large-scale operation, the steps of forming a biphasic solution and separating the organic phase from the aqueous phase, may be performed efficiently as steps of a continuous liquid-liquid extraction, or as steps in an overall, continuous extractive crystallization process. The steps of forming a biphasic solution and separating the organic phase from the aqueous phase may also be performed as steps of a multi-stage liquid-liquid extraction, or as steps in an overall, extractive crystallization process. Such extraction, or extractive crystallization process, may further comprise one or more additional stages of extracting the aqueous phase with additional extraction quantities of the organic phase, e.g., additional quantities of liquid having the composition of the organic phase, but not used in the organic phase itself initially. Processes may comprise extracting the aqueous phase in one or more extracting stages by contact with such one or more respective, additional extraction quantities of the organic phase to extract (or selectively solubilize) one or more respective, additional portions of the compound of interest (FDME or other diester of FDCA, originally present in the crude composition) from the aqueous phase. Following such extraction stages, the one or more additional extraction quantities of the organic phase may be combined with the organic phase, used initially in forming the biphasic solution, prior to crystallizing the purified composition from the resulting, combined organic phase. The one or more additional stages of extracting the aqueous phase can therefore serve to increase the yield of the compound of interest in the combined organic phase, and consequently its yield upon recovery following a subsequent crystallization stage.

Alternatively, or in combination, such extraction, or extractive crystallization process, may further comprise one or more additional stages of extracting the organic phase with additional extraction quantities of the aqueous phase, e.g., additional quantities of liquid having the composition of the aqueous phase, but not used in the aqueous phase itself initially. Processes may comprise extracting the organic phase in one or more extracting stages by contact with such one or more respective, additional extraction quantities of the aqueous phase to extract (or selectively solubilize) one or more respective, additional portions of one or more impurities present in the crude composition (e.g., one or more of impurities (i), (ii), (iii), and (iv) as described above) from the organic phase. Following such extraction stages, the one or more additional extraction quantities of the aqueous phase may be combined with the aqueous phase, used initially in forming the biphasic solution, prior to crystallizing the purified composition from the resulting, combined aqueous phase. The one or more additional stages of extracting the organic phase can therefore serve to increase the yield of the one or more impurities in the combined aqueous phase, and/or increase the purity of the compound of interest, following crystallization from the organic phase, or combined organic phase (in the case of using additional extraction quantities of the organic phase, as described above).

With respect to such processes that extract (selectively solubilize), either continuously or with one or more extraction stages, impurities of the crude composition in an aqueous phase or combined aqueous phase (in the case of using additional extraction quantities of the aqueous phase, as described above), the removal of such impurities that would otherwise manifest in the purified composition can improve its color and/or color stability, such as in the case of removing impurities according to (i) and/or (ii), described above. Alternatively, or in combination, the extraction of such impurities into the aqueous phase or combined aqueous phase can concentrate particular impurities, having value as partially converted and unconverted compounds, into this phase, such as in the case of concentrating impurities according to (iii) and/or (iv), described above. This can advantageously allow for such partially converted and unconverted compounds to be recycled to an esterification reactor, for their complete, or at least more complete, esterification.

In representative processes, for example, the aqueous phase may comprise a greater proportion, relative to the compound of interest (FDME or other diester of FDCA), than the organic phase, of impurities according to (iii) and/or (iv), described above (e.g., of partially esterified (partially converted) 2,5-furandicarboxylic acid, monomethyl ester (FDMME) and/or non-esterified (unconverted) 2,5-furandicarboxylic acid (FDCA), originally present in the crude composition. The aqueous phase may also, or otherwise, comprise a greater amount than the organic phase, of impurities according to (iii) and/or (iv), described above (e.g., of partially esterified (partially converted) 2,5-furandicarboxylic acid, monomethyl ester (FDMME) and/or non-esterified (unconverted) 2,5-furandicarboxylic acid (FDCA), originally present in the crude composition. According to particular embodiments, processes may further comprise utilizing impurities according to (iii) and/or (iv), described above (e.g., FDMME and/or FDCA), present in the aqueous phase, in an esterification reactor to convert at least a portion of such impurities to the compound of interest (e.g., FDME). For example, one or more of such impurities may be recycled to the same esterification reactor from which the crude composition is obtained.

Whether or not impurities according to (iii) and/or (iv), described above are ultimately utilized in (e.g., recycled to) an esterification reactor, they may be recovered from the aqueous phase (or combined aqueous phase) as valuable products, such that process economics are improved. The step of utilizing these impurities (e.g., FDMME and/or FDCA), for recycle to an esterification reactor or for another purpose, may comprise recovering at least a portion of these impurities, present in the aqueous phase (or combined aqueous phase), by separation from this phase. For example, processes may comprise recovering at least a portion of these impurities as a solid precipitate, and more specifically recovering this precipitate by filtration. In the case of impurities of value being present in the aqueous phase (e.g., in a sodium bicarbonate solution), these may be precipitated from this phase by changing a property of the aqueous phase that reduces their solubility, such as by lowering the pH of the aqueous phase to reduce the proportion of carboxylic acid groups of these impurities that are ionized.

Steps of forming a biphasic solution are not limited to those in which such a solution of the crude composition is formed. For example, according to processes in which two or more stages of crystallization are used, a second-stage biphasic solution of the purified composition may be formed, a third stage biphasic solution of the second-stage purified composition may be formed, etc. In other embodiments, a step of forming a biphasic solution of the crude composition may be omitted, but one or more steps of forming a biphasic solution of the purified composition and/or biphasic solutions of higher-stage purified compositions may be used, whereby the associated higher stage is rendered an extractive crystallization stage.

The use of a solid treatment medium to improve the quality of a solution of the crude composition is also contemplated, in various combinations with crystallization. An example would comprise dissolving the crude composition in a solvent to form a solution of the crude composition and contacting the solution of the crude composition with the solid treatment medium to provide a treated solution of the crude composition. The solvent may be as described above, and is not limited by excluding alcohols and may therefore comprise (e.g., in a predominant amount as described above), one or more compounds having at least one hydroxy (—OH) functional group, such as an alcohol, a diol, a polyol, and/or a glycol. A preferred solvent is methanol. A solid treatment medium may, for example, remove insoluble impurities, such as metals and their metallic salts as described above, from the solution of the crude composition, such that the treated solution has a reduced content of the insoluble impurities, relative to the solution of the crude composition. For this purpose, a solid treatment medium comprising diatomaceous earth (DE) is effective. A solid treatment medium may also or otherwise, for example, improve the color of the solution of the crude composition, such that the treated solution has a lighter color, relative to the solution of the crude composition. For this purpose, a solid treatment medium comprising carbon, such as activated carbon (AC) is effective. Such treatments, to reduce the content of insoluble impurities and/or improve color of the solution of the crude composition, likewise extend to the same improvements in the purified composition and/or higher-stage purified compositions.

The solution of the crude composition, following its formation, may be contacted with such a solid treatment medium either batchwise or continuously. For example, batchwise contacting may be carried out by mixing the solution of the crude composition with particles of the solid treatment medium and agitating (e.g., shaking, stirring, vibrating) the mixture, followed by filtering the mixture to separate the solid treatment medium and recover the treated solution. Continuous contacting may be carried out by passing (e.g., pumping) the solution of the crude composition through a fixed bed of the solid treatment medium, with the effluent from this bed corresponding to the treated solution.

In addition, steps of treating by contact with a solid treatment medium are not limited to treating the solution of the crude composition. For example, according to processes in which two or more stages of crystallization are used, such steps may comprise contacting a second-stage solution of the purified composition, a third stage solution of the second-stage purified composition, etc. In other embodiments, a step of treating by contacting the solution of the crude composition may be omitted, but one or more steps of contacting a solution of the purified composition and/or solutions of higher-stage purified compositions may be used. Steps of treating with a solid treatment medium to remove insoluble impurities and/or improve color, as described above, can be carried out in any order and may be used independently in various stages of processes utilizing two or more stages of crystallization.

For example, according to a particular embodiment, a representative process may comprise contacting the solution of the crude composition with a solid treatment medium, such as diatomaceous earth (DE) to remove insoluble impurities and provide the treated solution, having a reduced content of the insoluble impurities relative to the solution of the crude composition. In the case of using DE as the solid treatment medium with which the solution of the crude composition is contacted, subsequent stages of crystallization may omit the use of DE but instead use carbon (e.g., AC) to improve the color of a solution of the purified composition (recovered from the first stage), formed by dissolving this purified composition in a second-stage solvent (e.g., having the same or different composition relative to the solvent used to form the solution of the crude composition). Representative processes may therefore comprise recovering the purified composition (e.g., by filtration) and performing a second stage of purification (crystallization) comprising dissolving (or re-dissolving) the purified composition in a second-stage solvent to form a second-stage solution of the purified composition, and contacting the second-stage solution of the purified composition with a solid treatment medium, such as carbon (e.g., AC) to provide a second-stage treated solution, having a lighter color relative to the second-stage solution. These processes may further comprise crystallizing, from the second-stage treated solution, a second-stage purified composition having an increased content or percentage by weight of the compound of interest (FDME or other diester of FDCA), relative to both the purified composition and the crude composition. Additional stages of crystallization, with or without the contacting of solutions formed at these stages with a solid treatment medium, are also contemplated. Likewise, any stage(s) of crystallization can alternatively, or in combination, utilize a separate aqueous phase to form a biphasic solution as described above, such that any of such stage(s) is rendered an extractive crystallization stage.

Advantageously, crystallization processes described herein, optionally in combination with extraction and/or the use of a solid treatment medium as described herein, provide an effective and straightforward solution for the purification of solid compositions of FDME and other diesters of FDCA, particularly when compared to distillation. The processes afford favorable combinations of purity of the compound of interest and recovery (yield) of this compound, based on the quantity initially present in the crude composition. Following a single stage of crystallization, for example, the compound of interest (e.g., FDME) may be present in the purified composition at a purity that exceeds 98 wt-%, that exceeds 99 wt-%, or that even exceeds 99.8 wt-%. These purity levels, or even higher purity levels, are applicable to higher-stage purified compositions (e.g., a second-stage purified composition). Of further practical importance is the ability of processes described herein to provide purified compositions having very low levels of impurities according to (i) and/or (ii), described above, which even in very small quantities are detrimental in terms of their propensity to form color and/or decrease color stability in these compositions, as well as in bio-based polymers made from the use of these compositions in downstream polymerization. For example, either or both of impurities according to (i) (e.g., 5-formyl-2-furandicarboxylic acid (FFCA)) and (ii) (e.g., 5-formyl-2-furandicarboxylic acid methyl ester (FFME)) may be present, in a purified composition or higher-stage purified composition, in an amount of less than 500 wt-ppm, less than 100 wt-ppm, less than 50 wt-ppm, or even less than 10 wt-ppm. Any of these purity characteristics of purified compositions or higher-stage purified compositions, in terms of the presence of the compound of interest and/or the presence of undesired impurities, may be attained with a recovery of the compound of interest in a purified composition or higher-stage purified composition, representing at least 60 wt-% (e.g., from 60 wt-% to 99 wt-%), at least 70 wt-% (e.g., from 70 wt-% to 95 wt-%), or at least 75 wt-% (e.g., from 75 wt-% to 92 wt-%), of the compound of interest in the crude composition.

The following examples are set forth as representative of the present invention. These examples are illustrative and not to be construed as limiting the scope of the invention as defined in the appended claims.

Example 1

Solubility of a Crude Composition Comprising FDME in Various Solvents

An impure solid FDME sample, obtained from the esterification of FDCA with methanol, was determined to have 82.6 wt-% FDME (dimethyl ester), in addition to 10.4 wt-% of the monomethyl ester, FDMME, resulting from incomplete esterification. The sample also contained 0.35 wt-% of the FDCA starting compound and 0.58 wt-% of the aldehyde contaminant, FFME. In separate solubility studies with different solvents, various amounts of this sample were charged to a scintillation vial, and in each case 10 ml of solvent was added. The vial was then sonicated for 15 minutes at 35° C., and the solubility of FDME was determined. The results are given in Table 1 below.

TABLE 1

| Solubility of FDME in Various Solvents | | |
|---|---|---|
| Solvent | FDME solubility limits (wt-%) | Remarks |
| 1,1,2,2-tetrachloroethane | 23-27 | Very soluble |
| 1,3-Propanediol | <8 | Insoluble |
| 1,4-Dioxane | 23-28 | Very soluble |
| Acetone | 12-20 | Soluble |
| Acetonitrile | >39 | Exceptionally soluble |
| N,N'-dimethylformamide | 30-35 | Very soluble |
| Dimethyl sulfoxide | 9-13 | Soluble |
| Ethanol | <10 | Insoluble |
| Ethyl Acetate | 18-25 | Very soluble |
| Ethylene Glycol | <8 | Insoluble |
| Methanol | <11 | Insoluble |
| Methylene Chloride | 27-31 | Very soluble |
| Methyl-t-butyl ether | <10 | Insoluble |
| Pyridine | 17-23 | Very soluble |
| THF | 17-23 | Very soluble |
| Toluene | <10 | Insoluble |

From these results, it can be appreciated that crude compositions of FDME exhibit favorable solubility in methylene chloride; acetonitrile; N,N'-dimethylformamide; 1,4-dioxane; 1,1,2,2-tetrachloroethane; ethyl acetate; tetrahydrofuran; pyridine; acetone; and dimethyl sulfoxide.

Example 2

Extractive Crystallization of FDME from a Crude Composition, Using a Biphasic Solution Having Methylene Chloride as an Organic Phase and Sodium Bicarbonate as an Aqueous Phase A 200 gram sample of a dried, impure mixture (crude composition comprising FDME) obtained from the esterification of FDCA with methanol to FDME was added to a 500 ml Erlenmeyer flask equipped with a PTFE magnetic stir bar. This solid composition was determined by UPLC-PDA to be 80 wt-% FDME, 18 wt-% FDMME, and 2 wt-% FDCA. Approximately 100 ml of methylene chloride was added to the flask, followed by 100 ml of 5 wt-% sodium bicarbonate. The biphasic solution was vigorously stirred for 30 minutes and transferred to a 1 liter separatory flask, which was used to remove the bottom organic phase. The top aqueous phase was extracted 2 times with additional extraction quantities, 30 ml each, of methylene chloride. These additional extraction quantities were combined with the organic phase, and the combined liquids were transferred to a 500 ml Wheaton bottle and placed in the freezer overnight. The following morning, this storage bottle was removed from the freezer, revealing a profusion of long, shard-like crystals, which were filtered with a Buchner funnel. The retained crystals were dried with a stream of argon for 1 hour, determined to have a weight of 58.7 grams, and then stored in a 250 ml Wheaton bottle. A purity analysis of the crystals of the purified composition was carried out by quantitative $^1$H NMR, indicating these to be 99.98 wt-% pure. The crystals were stored in ambient air and in a bottle on a tabletop. This very high purity was surprisingly maintained after 3.5 years, demonstrating the exceptional stability of the purified composition. Moreover, this composition retained its characteristics over this time period, in terms of comprising free-flowing crystals with very little development of off-white color.

In this regard, the color of the purified FDME composition was evaluated quantitatively by determining its chromaticity coordinates in the L*a*b* color space. This refers to a particular color space of different color systems of the CIE, or Commission Internationale de l'Echairage (International Commission of Illumination), which color systems were developed as a way to standardize color, or express color values numerically, and thereby remove the subjectivity of the human observer. The CIE 1976 (L*a*b*) color space is based on the opponent-colors theory of color vision, according to which two colors cannot be both green and red at the same time, nor blue and yellow at the same time. Therefore, single values can be used to describe the red/green and the yellow/blue attributes of a sample. In this regard, when a color is expressed using the L a*b* color space, the respective coordinates of L*, a*, and b* denote lightness, the red/green value, and the yellow/blue value, with these coordinates ranging from −100 to +100. For purposes of characterizing compositions described herein with respect to yellow color, the value of b* is particularly relevant. The assessment of the L*, a*, and b* coordinates of the purified FDME composition was performed using a commercially available colorimeter from Konica Minolta, model CM-5.

Another color measurement, which is referred to as APHA color, was also determined for the purified FDME composition according to ASTM D1209. APHA color is also known as the Hazen scale, as well as the platinum cobalt (Pt/Co) scale. APHA is a color standard named for the American Public Health Association that was originally intended to describe the color of wastewater, but its usage has expanded to include other applications. APHA color is a color scale sometimes referred to as a "yellowness index" that is used to assess the quality of liquids that are clear to yellowish in color.

To prepare a first sample, Sample #1, of the purified FDME composition for color analysis, a 0.597 gram portion of the composition was dissolved in 9.414 grams of a solvent mixture of 1:1 (v/v) acetonitrile/isopropanol, such that Sample #1 contained 5.96 wt-% of the dissolved composition. A second sample, Sample #2 was prepared by dissolving a 0.592 gram portion of the composition in 9.406 grams of this solvent, such that Sample #2 contained 5.92 wt-% of the dissolved composition. For each sample having a target concentration of 6 wt-% dissolved solids, two CIE 1976 (L*a*b*) colorimetry measurements and two APHA measurements were performed. The samples and results are summarized in Tables 2 and 3 below.

TABLE 2

| Samples of Purified FDME for Colorimetry Analysis | | | | |
|---|---|---|---|---|
| | SAMPLE #1 | | SAMPLE #2 | |
| | mass (g) | wt-% | mass (g) | wt-% |
| FDME | 0.597 | 5.96 | 0.592 | 5.92 |
| Solvent | 9.414 | 94.04 | 9.406 | 94.08 |

TABLE 3

| Colorimetry/APHA Results | | | | |
|---|---|---|---|---|
| | L* | a* | b* | Hazen/APHA |
| Solvent | 100 | 0 | −0.01 | 0 |
| Sample #1, Measurement 1 | 99.40 | −0.03 | 0.38 | 11 |
| Sample #1, Measurement 2 | 99.42 | −0.01 | 0.36 | 10 |
| Sample #2, Measurement 1 | 99.46 | −0.01 | 0.40 | 12 |
| Sample #2, Measurement 2 | 99.44 | 0.01 | 0.39 | 12 |
| Average | 99.43 | −0.01 | 0.39 | 12 |

The above results are indicative of remarkable color stability, insofar as the purified FDME composition (crystallized from methylene chloride) was stored for over 3 years with no special handling, i.e., with exposure to ambient air. Even after the elapsed time, the colorimetry results met specifications for purified FDME of L*>99, a*<0.5, and b*<0.5.

Example 3

Crystallization of FDME from a Crude Composition, Using DE as a Solid Treatment Medium The combination of filtration with diatomaceous earth and crystallization was investigated for its effectiveness in purifying a crude composition of FDME, having weight percentages of individual compounds as described in Example 1. A 105 gram sample of this crude composition was ground and dissolved in 700 ml of methanol to provide a 15 wt-% stock solution of the crude composition, which was maintained at 55° C. in a water bath with shaking. A 300 gram portion of this stock solution was removed and diluted to 2 wt-% dissolved solids, or approximately the room temperature solubility, and filtered on a 2" diatomaceous earth (DE) filter using a Buchner funnel. Following this DE filtration, the solution was concentrated back to 20 wt-% in a crystallizer using a vacuum pump to evaporate the methanol solvent. Starting at a temperature of 50° C., cooling crystallization was performed, without the need for seeding, as primary nucleation occurred rapidly upon cooling. Stirring at 100 rpm was maintained during the cooling, and the particle size distribution was determined in real time. A programmed cooling profile was used to attain a solution temperature of 10° C. over a 20-hour period with varying amounts of residence time at different temperatures. It was determined that a 2-hour residence time at 35° C. and subsequent cooling to 30° C. leads to significant nucleation. Following a 2-hour residence time at 30° C., crystal growth became significant, with the number of fine crystals decreasing at approximately the same rate as the rate of increase in the number of large (>100 micron) crystals. Growth of the initial, fine crystals was evidenced by the total crystal count remaining stable. This growth continued with slow cooling at 1.7° C./hr, over a time period in which crystal weight increased by 25%. As crystallization progressed, the crystal size distribution narrowed as the mean crystal diameter increased.

The solids from crystallization were emptied onto a Buchner funnel filter, and the crystals were sprayed with room temperature methanol. The mother liquor from the filtration contained approximately 2 wt-% FDME, corresponding to its room temperature solubility in methanol. However, since only fine crystals re-dissolve when the 10° C. crystallized solids/methanol mixture is warmed to room temperature, crystal growth is an important factor in achieving high yield/recovery. The spraying with methanol was discontinued when the wash methanol was light in color, indicating that impurities were no longer being removed. Following this single stage of crystallization, 67% of the FDME from the crude composition was recovered in the purified composition, which was determined to be 99.05 wt-% FDME and 0.86 wt-% FDMME. It is also possible to capture the 2-4 wt-% of FDME remaining in the mother liquor/wash methanol. In any event, favorable purity and recovery characteristics were therefore obtained.

Example 4

Crystallization of FDME from a Crude Composition, Using DE as a Solid Treatment Medium, Fast Cooling Additional experiments were performed as described in Example 3, but with cooling from 65° C. to 15° C. being performed more rapidly over 6-hour and 2-hour periods. These experiments also led to the recovery of crystals having >99 wt-% FDME purity, but also having a smaller mean size that led to a lower yield (greater loss in the wash methanol as described in Example 3). The purified composition obtained following the 6-hour period was 99.20 wt-% FDME and 0.76 wt-% FDMME, whereas the composition obtained following the 2-hour period was 99.06 wt-% FDME and 0.90 wt-% FDMME. Again, high purity was achieved in a single stage, and the additional experiments demonstrated the tradeoff between cooling time and recovery.

Example 5

Crystallization of FDME from a Crude Composition, Using AC as a Solid Treatment Medium Additional experiments were performed as described in Example 3, but using AC as a solid treatment medium, rather than DE. In particular, the methanol solution of the crude composition described in this example was treated with 5 wt-% AC, followed by cooling, crystallization, and methanol washing as described in this example. Importantly, the yield or recovery of FDME from the crude composition following this single stage of crystallization was 84.1%, and the crystals were considerably whiter in color, compared to those recovered in Example 3. The purity of these crystals was determined to be 99.56 wt-%. Another significant result of this experiment was that no FDME was lost in the activated carbon treatment step, i.e., 100% was recovered, despite the fact that isotherm carbon studies on pure FDME indicated some losses of furan rings. Without being bound by theory, it is believed that competing impurities in the crude composition of FDME mitigated this effect. This single stage of crystallization with activated carbon pretreatment advantageously resulted in a beneficial combination of product purity, recovery, and appearance.

Specific embodiments and examples described herein are for illustrative purposes, and not limiting of the invention as set forth in the appended claims. The practice of the present invention further relates to all beneficial effects that are inherent in this practice. Those having skill in the art, with the knowledge gained from the present disclosure, will recognize that various changes can be made to the disclosed processes, in attaining the advantages described herein and other advantages, without departing from the scope of the present disclosure.

Items:

1. A process for purifying a crude composition comprising 2,5-furandicarboxylic acid, dimethyl ester (FDME), the process comprising:
   dissolving the crude composition in a non-methanol solvent to form a solution of the crude composition, and
   crystallizing, from the solution of the crude composition, a purified composition having an increased content of FDME relative to the crude composition.
2. The process of item 1, wherein the crude composition comprises FDME in an amount from 75 wt-% to 95 wt-%.
3. The process of item 1, wherein the non-methanol solvent is an organic solvent.
4. The process of item 1, wherein the non-methanol solvent is a non-alcohol solvent.

5. The process of any of items 1 through 4, wherein a non-methanol solvent is employed in which FDME has a solubility at 35° C. of at least 12 wt-%.

6. The process of item 1, wherein the non-methanol solvent comprises a halogenated hydrocarbon, a nitrile, an amide, a heterocyclic ring-containing compound, an acetate, a ketone, or a sulfoxide.

7. The process of item 1, wherein the non-methanol solvent comprises a compound selected from the group consisting of methylene chloride; acetonitrile; N,N'-dimethylformamide; 1,4-dioxane; 1,1,2,2-tetrachloroethane; ethyl acetate; tetrahydrofuran; pyridine; acetone; and dimethyl sulfoxide.

8. The process of any of items 1 through 7, wherein the solution of the crude composition is formed at an elevated temperature from 25° C. to the normal boiling point of the non-methanol solvent.

9. The process of item 8, wherein the steps of dissolving and crystallizing are carried out at a temperature of less than 100° C.

10. The process of any of items 1 through 9, wherein the step of crystallizing comprises cooling the solution of the crude composition.

11. The process of item 1, wherein the purified composition has a decreased content of one or more impurities selected from the group consisting of 2,5-furandicarboxylic acid, monomethyl ester (FDMME); 2,5-furan dicarboxylic acid (FDCA); 5-formyl-2-furancarboxylic acid methyl ester (FFME); 5-formyl-2-furancarboxylic acid (FFCA); and methyl 2-furoate (MF), relative to the crude composition.

12. A process for purifying a crude composition comprising 2,5-furandicarboxylic acid, dimethyl ester (FDME), the process comprising:
forming a biphasic solution of the crude composition in a solvent comprising an organic phase and a separate aqueous phase,
separating the organic phase from the aqueous phase, and
crystallizing, from the organic phase, a purified composition having an increased content of FDME relative to the crude composition.

13. The process of item 12, wherein the steps of forming a biphasic solution and separating the organic phase from the aqueous phase are steps of a continuous liquid-liquid extraction, wherein one or more impurities in the crude composition are selectively solubilized in the aqueous phase, relative to FDME in the crude composition, and wherein FDME is selectively solubilized in the organic phase, relative to one or more impurities in the crude composition.

14. The process of item 12, wherein the steps of forming a biphasic solution and separating the organic phase from the aqueous phase are steps of a multi-stage liquid-liquid extraction, wherein the process further comprises:
extracting the aqueous phase in one or more extracting stages by contact with one or more respective, additional extraction quantities of the organic phase to extract one or more respective, additional portions of FDME from the aqueous phase; and
combining the one or more additional extraction quantities of the organic phase, comprising the one or more respective, additional portions of FDME, with the organic phase, prior to crystallizing, from a combined organic phase, the purified composition.

15. The process of item 12, wherein the aqueous phase comprises a greater proportion, relative to FDME, than the organic phase, of partially esterified 2,5-furandicarboxylic acid, monomethyl ester (FDMME) and/or non-esterified 2,5-furan dicarboxylic acid (FDCA), and wherein the process further comprises:
utilizing FDMME and/or FDCA, present in the aqueous phase, in an esterification reactor to convert at least a portion of the FDMME and/or FDCA to FDME.

16. The process of item 15, wherein the step of utilizing FDMME and/or FDCA comprises recovering at least a portion of the FDMME and/or FDCA, present in the aqueous phase, as a solid precipitate.

17. A process for purifying a crude composition comprising 2,5-furandicarboxylic acid, dimethyl ester (FDME), the process comprising:
dissolving the crude composition in a solvent to form a solution of the crude composition,
contacting the solution of the crude composition with a solid treatment medium to provide a treated solution, and
crystallizing, from the treated solution of the crude composition, a purified composition having an increased content of FDME relative to the crude composition.

18. The process of item 17, wherein the solid treatment medium removes insoluble impurities from the solution of the crude composition.

19. The process of item 17, wherein the solid treatment medium improves the color of the solution of the crude composition.

20. The process of item 17, further comprising recovering the purified composition and performing a second stage of purification comprising:
dissolving the purified composition in a second-stage solvent to form a second-stage solution of the purified composition,
contacting the second-stage solution of the purified composition with a solid treatment medium to provide a second-stage treated solution, having a lighter color relative to the second-stage solution, and
crystallizing, from the second-stage treated solution, a second-stage purified composition having an increased content of FDME relative to both the purified composition and the crude composition.

What is claimed is:
1. A process for purifying a crude composition comprising 2,5-furandicarboxylic acid, dimethyl ester (FDME), the process comprising:
forming a biphasic solution of the crude composition in a solvent comprising an organic phase and a separate aqueous phase,
separating the organic phase from the aqueous phase, and
crystallizing, from the organic phase, a purified composition having an increased content of FDME relative to the crude composition,
wherein the steps of forming a biphasic solution and separating the organic phase from the aqueous phase are steps of a continuous liquid-liquid extraction, wherein one or more impurities in the crude composition are selectively solubilized in the aqueous phase, relative to FDME in the crude composition, and wherein FDME is selectively solubilized in the organic phase, relative to one or more impurities in the crude composition.

2. The process of claim 1, wherein the crude composition comprises FDME in an amount from 75 wt-% to 95 wt-%.

3. The process of claim 1, wherein the solution of the crude composition is formed at an elevated temperature from 25° C. to the normal boiling point of the compound in the solution having the lowest boiling point.

4. The process of claim 3, wherein the steps of dissolving and crystallizing are carried out at a temperature of less than 100° C.

5. The process of claim 1, wherein the step of crystallizing comprises cooling the solution of the crude composition.

6. The process of claim 1, wherein the steps of forming a biphasic solution and separating the organic phase from the aqueous phase are steps of a multi-stage liquid-liquid extraction, wherein the process further comprises:

extracting the aqueous phase in one or more extracting stages by contact with one or more respective, additional extraction quantities of the organic phase to extract one or more respective, additional portions of FDME from the aqueous phase; and combining the one or more additional extraction quantities of the organic phase, comprising the one or more respective, additional portions of FDME, with the organic phase, prior to crystallizing, from a combined organic phase, the purified composition.

7. The process of claim 1, wherein the aqueous phase comprises a greater proportion, relative to FDME, than the organic phase, of partially esterified 2,5-furandicarboxylic acid, monomethyl ester (FDMME) and/or non-esterified 2,5-furan dicarboxylic acid (FDCA), and wherein the process further comprises:

utilizing FDMME and/or FDCA, present in the aqueous phase, in an esterification reactor to convert at least a portion of the FDMME and/or FDCA to FDME.

8. The process of claim 7, wherein the step of utilizing FDMME and/or FDCA comprises recovering at least a portion of the FDMME and/or FDCA, present in the aqueous phase, as a solid precipitate.

9. A process for purifying a crude composition comprising 2,5-furandicarboxylic acid, dimethyl ester (FDME), the process comprising:

dissolving the crude composition in a solvent to form a solution of the crude composition, contacting the solution of the crude composition with a solid treatment medium comprising diatomaceous earth and/or activated carbon to provide a treated solution, and crystallizing, from the treated solution of the crude composition, a purified composition having an increased content of FDME relative to the crude composition.

10. The process of claim 9, further comprising recovering the purified composition and performing a second stage of purification comprising:

dissolving the purified composition in a second-stage solvent to form a second-stage solution of the purified composition, contacting the second-stage solution of the purified composition with a solid treatment medium to provide a second-stage treated solution, having a lighter color relative to the second-stage solution, and crystallizing, from the second-stage treated solution, a second-stage purified composition having an increased content of FDME relative to both the purified composition and the crude composition.

11. The process of claim 9, wherein the crude composition comprises FDME in an amount from 75 wt-% to 95 wt-%.

12. The process of claim 9, wherein the solution of the crude composition is formed at an elevated temperature from 25° C. to the normal boiling point of the compound in the solution having the lowest boiling point.

13. The process of claim 12, wherein the steps of dissolving and crystallizing are carried out at a temperature of less than 100° C.

14. The process of claim 9, wherein the step of crystallizing comprises cooling the solution of the crude composition.

15. The process of claim 9, wherein the solution of the crude composition is formed at an elevated temperature from 25° C. to 100° C.

\*    \*    \*    \*    \*